US011763936B2

(12) United States Patent
Co et al.

(10) Patent No.: US 11,763,936 B2
(45) Date of Patent: *Sep. 19, 2023

(54) GENERATING STRUCTURED TEXT CONTENT USING SPEECH RECOGNITION MODELS

(71) Applicant: Google LLC, Mountain View, CA (US)

(72) Inventors: Christopher S. Co, Saratoga, CA (US); Navdeep Jaitly, Mountain View, CA (US); Lily Hao Yi Peng, Mountain View, CA (US); Katherine Irene Chou, Palo Alto, CA (US); Ananth Sankar, Palo Alto, CA (US)

(73) Assignee: Google LLC, Mountain View, CA (US)

( * ) Notice: Subject to any disclaimer, the term of this patent is extended or adjusted under 35 U.S.C. 154(b) by 119 days.

This patent is subject to a terminal disclaimer.

(21) Appl. No.: 17/112,279

(22) Filed: Dec. 4, 2020

(65) Prior Publication Data

US 2021/0090724 A1    Mar. 25, 2021

Related U.S. Application Data

(63) Continuation of application No. 15/362,643, filed on Nov. 28, 2016, now Pat. No. 10,860,685.

(51) Int. Cl.
*G10L 15/26* (2006.01)
*G16H 40/20* (2018.01)
(Continued)

(52) U.S. Cl.
CPC ............ *G16H 40/20* (2018.01); *G06F 40/47* (2020.01); *G06F 40/58* (2020.01); *G10L 15/063* (2013.01);
(Continued)

(58) Field of Classification Search
CPC ..... G10L 15/22; G10L 15/183; G10L 15/063; G10L 15/26; G10L 15/193; G10L 15/265; G10L 15/1822; G10L 14/142; G10L 15/16

See application file for complete search history.

(56) References Cited

U.S. PATENT DOCUMENTS 7,668,718 B2   2/2010 Kahn
9,190,050 B2 *  11/2015 Mathias ................ G16H 15/00
(Continued)

FOREIGN PATENT DOCUMENTS

CN    104380375 A    2/2015
EP      1787288 A2    5/2007
(Continued)

OTHER PUBLICATIONS

Azzini et al. "Application of Spoken Dialogue Technology in a Medical Domain," Text, Speech and Dialogue, Springer Berlin Heidelberg, vol. 2448, Jan. 1, 2006, 4 pages.
(Continued)

*Primary Examiner* — Vijay B Chawan
(74) *Attorney, Agent, or Firm* — Fish & Richardson P.C.

(57) ABSTRACT

Methods, systems, and apparatus, including computer programs encoded on computer storage media for speech recognition. One method includes obtaining an input acoustic sequence, the input acoustic sequence representing one or more utterances; processing the input acoustic sequence using a speech recognition model to generate a transcription of the input acoustic sequence, wherein the speech recognition model comprises a domain-specific language model; and providing the generated transcription of the input acoustic sequence as input to a domain-specific predictive model to generate structured text content that is derived from the transcription of the input acoustic sequence.

20 Claims, 4 Drawing Sheets

(51) Int. Cl.
*G10L 15/18* (2013.01)
*G06F 40/47* (2020.01)
*G06F 40/58* (2020.01)
*G10L 15/06* (2013.01)
*G10L 15/14* (2006.01)
*G10L 15/16* (2006.01)
*G10L 15/183* (2013.01)

(52) U.S. Cl.
CPC ............ *G10L 15/142* (2013.01); *G10L 15/16* (2013.01); *G10L 15/183* (2013.01); *G10L 15/1822* (2013.01); *G10L 15/26* (2013.01)

(56) References Cited

U.S. PATENT DOCUMENTS

| | | | |
|---|---|---|---|
| 9,569,593 | B2* | 2/2017 | Casella dos Santos ..................... G16H 15/00 |
| 9,785,753 | B2 | 10/2017 | Casella dos Santos |
| 9,966,066 | B1* | 5/2018 | Corfield ................ G10L 15/142 |
| 10,199,124 | B2 | 2/2019 | Casella dos Santos |
| 10,283,110 | B2* | 5/2019 | Bellegarda ............ G10L 15/063 |
| 10,296,160 | B2* | 5/2019 | Shah ...................... G06F 3/0481 |
| 10,339,937 | B2 | 7/2019 | Koll et al. |
| 10,860,685 | B2* | 12/2020 | Co ......................... G10L 15/063 |
| 2002/0072896 | A1 | 6/2002 | Roberge et al. |
| 2002/0087357 | A1 | 7/2002 | Singer |
| 2003/0182117 | A1 | 9/2003 | Monchi et al. |
| 2004/0019482 | A1 | 1/2004 | Holub |
| 2006/0041428 | A1 | 2/2006 | Fritsch et al. |
| 2006/0149558 | A1* | 7/2006 | Kahn ..................... G10L 15/063 704/278 |
| 2009/0326937 | A1 | 12/2009 | Chitsaz et al. |
| 2010/0088095 | A1 | 4/2010 | John |
| 2012/0323574 | A1* | 12/2012 | Wang ..................... G16H 15/00 704/254 |
| 2013/0238312 | A1* | 9/2013 | Waibel .................. G06F 40/117 704/8 |
| 2013/0238330 | A1* | 9/2013 | Casella dos Santos ..................... G16H 10/60 704/235 |
| 2014/0019128 | A1* | 1/2014 | Riskin .................... G16H 10/60 704/235 |
| 2014/0249818 | A1* | 9/2014 | Yegnanarayanan ... G10L 15/193 704/244 |
| 2014/0324477 | A1 | 10/2014 | Oez |
| 2016/0078661 | A1 | 3/2016 | Iurascu |
| 2016/0196821 | A1 | 7/2016 | Yegnanarayanan |
| 2017/0116392 | A1 | 4/2017 | Casella dos Santos |

FOREIGN PATENT DOCUMENTS

| | | |
|---|---|---|
| JP | 2008136646 A | 6/2008 |
| JP | 2009541800 A | 11/2009 |
| WO | WO 2006023622 A2 | 3/2006 |

OTHER PUBLICATIONS

Chan et al., "Listen, Attend and Spell," (Aug. 20, 2015) [online] (retrieved from https://arxiv.org/pdf/1508.01211v2.pdf), 16 pages.

EP Office Action in European Application No. 17811802, dated Jul. 8, 2020, 6 pages.

Graves et al., Hybrid Speech Recognition with Bidirectional LSTM (2013) [online] (retrieved from http://www.cs.toronto.edu/~graves/asru_2013_poster.pdf) 1 page.

International Search Report and Written Opinion issued in International Application No. PCT/US2017/063301, dated Feb. 8, 2018, 15 pages.

Nguyen et al., "Deepr: A Convolutional Net for Medical Records," (Jul. 26, 2016) [online] (retrieved from https://arxiv.org/pdf/1607.07519v1.pdf), 9 pages.

PCT International Preliminary Report on Patentability in International Appln. No. PCT/US2017/063301, dated Jun. 6, 2019, 15 pages.

Shang et al., "Neural Responding Machine for Short-text Conversation," Proceedings of the 53rd Annual Meeting of the Association for Computational Linguistics and the 7th International Joint Conference on National Language Processing, pp. 1577-1586, Beijing China, Jul. 26-31, 2015; © 2015 Association for Computational Linguistics.

Shriberg and Stolcke, "Prosody Modeling for Automatic Speech Recognition and Understanding," (Nov. 28, 2016) [online] (retrieved from http://www.icsi.berkeley.edu/pubs/speech/prosodymodeling.pdf), 10 pages.

Sordoni et al., "A Neural Network Approach to Context-sensitive Generation of Conversational Responses," Human Language Technologies: The 2015 Annual Conference of the North American Chapter of the ACL, pp. 196-205, Denver, Colorado, May 31-Jun. 5, 2015; © 2015 Association for Computational Linguistics.

Vinyals and Le, "A Neural Conversational Model," (Jul. 22, 2015) [online] (retrieved from https://arxiv.org/pdf/1506.05869.pdf), 8 pages.

Wolk and Marasek, "Neural-based Machine Translation for Medical Text Domain. Based on European Medicines Agency Leaflet Texts," (Nov. 28, 2016) [online] (retrieved from https://arxiv.org/ftp/arxiv/papers/1509/1509.08644.pdf), 6 pages.

Office Action in Chinese Appln. No. 201780073503.3, dated Dec. 2, 2022, 33 pages (with English Translation).

* cited by examiner

GENERATING STRUCTURED TEXT CONTENT USING SPEECH RECOGNITION MODELS

CROSS REFERENCE TO RELATED APPLICATION

This application is a continuation of U.S. application Ser. No. 15/362,643, filed Nov. 28, 2016, the contents of which are incorporated by reference herein.

BACKGROUND

This specification relates to speech recognition systems.

Speech recognition systems receive an acoustic sequence and generate a transcription of an utterance represented by the acoustic sequence. Some speech recognition systems include a pronunciation system, an acoustic modeling system and a language model. The acoustic modeling system generates a phoneme representation of the acoustic sequence, the pronunciation system generates a grapheme representation of the acoustic sequence from the phoneme representation, and the language model generates the transcription of the utterance that is represented by the acoustic sequence from the grapheme representation.

SUMMARY

This specification describes systems and methods for generating formatted documents directly from audio recordings. For example, physician notes and patient instructions may be generated using an audio recording of a conversation between a patient and a medical professional.

In general, one innovative aspect of the subject matter described in this specification can be embodied in methods that include the actions of obtaining an input acoustic sequence, the input acoustic sequence representing one or more utterances; processing the input acoustic sequence using a speech recognition model to generate a transcription of the input acoustic sequence; and providing the generated transcription of the input acoustic sequence as input to a domain-specific predictive model to generate structured text content that is derived from the transcription of the input acoustic sequence.

Other embodiments of this aspect include corresponding computer systems, apparatus, and computer programs recorded on one or more computer storage devices, each configured to perform the actions of the methods. A system of one or more computers can be configured to perform particular operations or actions by virtue of software, firmware, hardware, or any combination thereof installed on the system that in operation may cause the system to perform the actions. One or more computer programs can be configured to perform particular operations or actions by virtue of including instructions that, when executed by data processing apparatus, cause the apparatus to perform the actions.

The foregoing and other embodiments can each optionally include one or more of the following features, alone or in combination. In some implementations the speech recognition model comprises a domain-specific language model.

In some implementations the domain-specific language model comprises a medical language model that has been trained using medical-specific training data.

In some implementations the domain-specific predictive model comprises a summarization predictive model that is configured to generate a physician note that is derived from the transcription of the input acoustic sequence.

In some implementations the summarization predictive model is further configured to generate a physician note that is derived from the transcription of the input acoustic sequence and one or more of (i) the input acoustic sequence, (ii) data associated with the input acoustic sequence, (iii) an acoustic sequence representing a physician dictation, or (iv) data representing a patient's medical record.

In some implementations the physician note comprises a document with a particular document format.

In some implementations the physician note comprises information that the summarization predictive model has extracted from the transcription of the input acoustic sequence based on the document format.

In some implementations the physician note comprises information that the summarization predictive model has extracted from the transcription of the input acoustic sequence and augmented based on the document format.

In some implementations the domain-specific predictive model comprises an automated billing predictive model that is configured to generate a bill based on the transcription of the input acoustic sequence.

In some implementations the automated billing predictive model is further configured to generate a bill that is based on the transcription of the input acoustic sequence and one or more of (i) the input acoustic sequence, (ii) data associated with the input acoustic sequence, (iii) an acoustic sequence representing a physician dictation, or (iv) data representing a patient's medical record.

In some implementations the domain-specific predictive model comprises a patient instruction predictive model that is configured to generate patient instructions that are derived from the transcription of the input acoustic sequence.

In some implementations the patient instruction predictive model is further configured to generate patient instructions that are derived from the transcription of the input acoustic sequence and one or more of (i) the input acoustic sequence, (ii) data associated with the input acoustic sequence, (iii) an acoustic sequence representing a physician dictation, or (iv) data representing a patient's medical record.

In some implementations the method further comprises providing the input acoustic sequence as input to a speech prosody detection predictive model to generate an indication of speech prosody that is derived from the input acoustic sequence.

In some implementations the domain-specific predictive model comprises a translation model that is configured to translate the transcription of the input acoustic sequence into a target language.

In some implementations the translation model is further configured to translate the transcription of the input acoustic sequence into a target language using the input acoustic sequence.

The subject matter described in this specification can be implemented in particular embodiments so as to realize one or more of the following advantages.

A system generating structured text content using speech recognition models, as described in this specification, may be used to generate clear, concise, complete, organized, and accurate text. For example, a healthcare provider generating physician notes using speech recognition models may be able to ensure that all generated physician notes include essential information, and that the information included is clearly and concisely presented. In this manner, all important and relevant information may be efficiently and effectively documented, thus contributing to an improvement in the quality and reliability of healthcare provided by the healthcare provider, and an improvement in patient safety.

A system generating structured text content using speech recognition models, as described in this specification, may improve the efficiency and computational resources required by a healthcare provider. For example, by generating important documents such as physician notes directly from a recording of a patient—medical professional conversation, the medical professional may not need to record a separate physician dictation. By avoiding the need for the medical professional to record a physician dictation or to enter notes while examining the patient, the medical professional's time may be saved and put to better use, focusing on patient care. For example, by connecting specific time points in an audio recording with generated physician notes, a medical professional may only be required to validate automatically generated notes. In addition, computational resources required by the healthcare provider may be reduced since physician dictations are not required to be saved or analyzed.

A system generating structured text content using speech recognition models, as described in this specification, may provide different types of information to assist the documentation of reimbursable activities, e.g., time-based services, quantities, or measurements. For example, using the system described in this specification, time stamped medical services can be extracted from an audio recording for reimbursement purposes.

A system generating structured text content using speech recognition models, as described in this specification, may be used to automatically generate important documents or checklists. For example, in many situations a medical professional may be required to determine a patient's history of present illness (HPI) and a review of systems (ROS). The system may be used to analyze a patient—medical professional conversation and to detect certain hotwords that are spoken by the patient and/or medical professional, e.g., hotwords such as HEENT, Neck, Cardiovascular, Respiratory, Gastrointestinal, Genitourinary, Musculoskeletal, Integumentary, Neurological, Psychiatric, Endocrine, Hematologic/Lymphatic, Allergic/Immunologic. The system may use detected hotwords to generate a checklist for a ROS.

A system generating structured text content using speech recognition models, as described in this specification, may be used to generate salient and more accurate medical notes for reimbursement documents that require chronic patients to include their disease diagnosis at every visit. Similarly, for reimbursement purposes it may sometimes be required to document all medications that a patient is currently taking and to update the document accordingly. The system described in this specification may assist with generating reimbursement documents by analyzing a combination of the patient's past medical history with the current clinical visit event, e.g., as captured by audio recordings.

A system generating structured text content using speech recognition models, as described in this specification, may apply speaker diarisation to enhance the readability of a generated speech transcription by structuring a received audio recording into speaker turns. Diarisation of speakers can enable the system to efficiently and accurately document a chief complaint as described in a patient's own words. In addition, a medical professional's verbal instructions can be electronically authorized, e.g., for the purposes of verifying a medical order (labs or medication) and also for reimbursement confirmation.

A system generating structured text content using speech recognition models, as described in this specification, may assist medical research and may lead to improvements in medical research. For example, by associating an audio recording with medical outcomes or medical events and patient diagnosis or prognosis, research in connecting prosody of speech with diseases may be more accurate.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

In many domain specific settings, interactions between people are required to be officially documented. For example, in a medical setting, interactions between patients and medical professionals may be summarized in a physician note. Typically, a physician note may be generated on behalf of the medical professional by a human scribe.

This specification describes systems and methods for generating domain specific structured text content, e.g., physician notes, directly from an audio recording of a conversation, e.g., between a patient and a medical professional. A speech recognition system may generate a transcription of the conversation. The generated transcription may be provided to one or more predictive models that generate structured text content, e.g., in the form of physician notes, based on the received transcription. Additional inputs may be provided to the one or more predictive models to supplement information in a generated transcript, e.g., a patient's medical history or a physician dictation.

Figure 1:
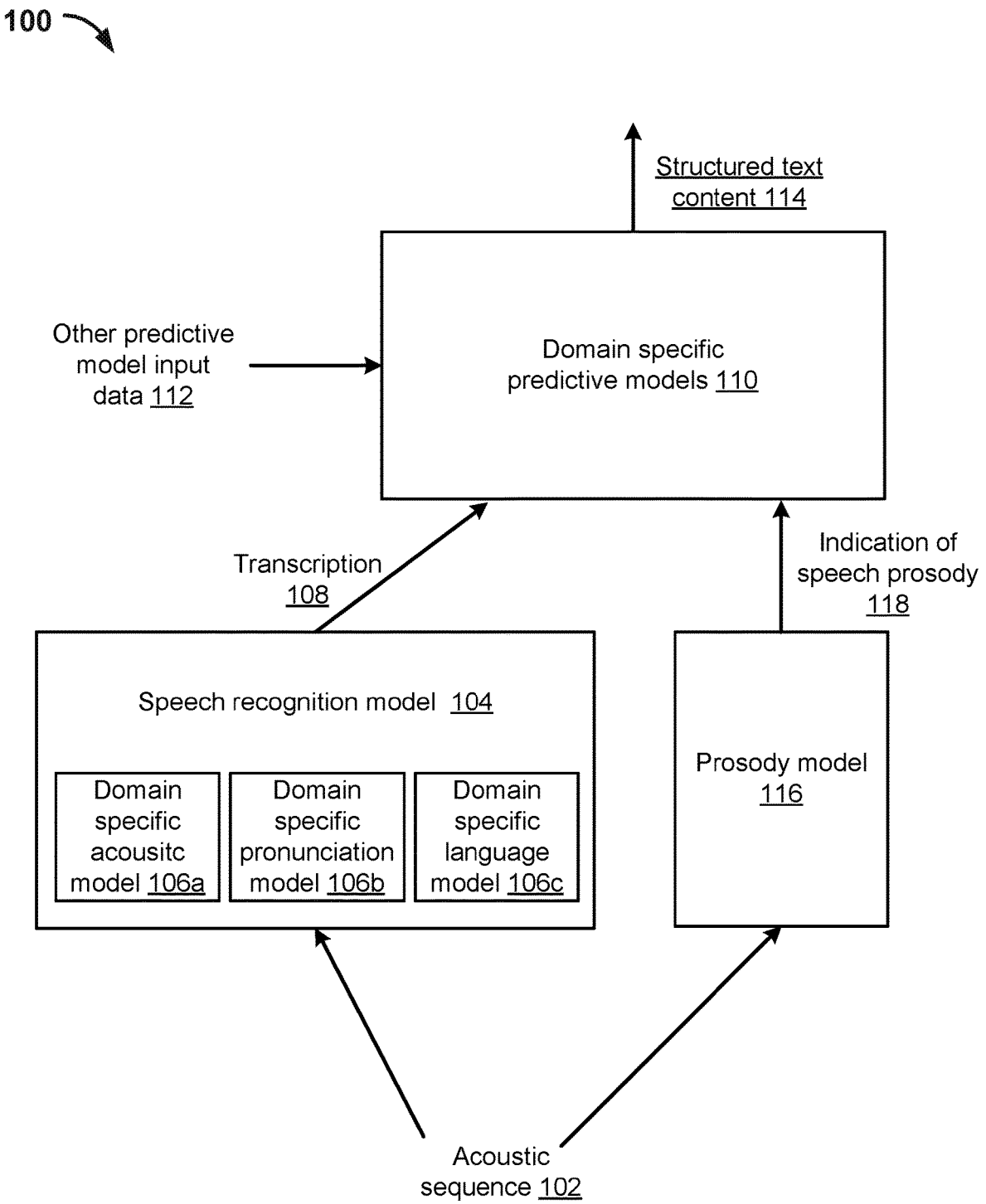
FIG. 1 shows an example system for generating structured text content using speech recognition models.

FIG. 1 shows an example domain specific text generator system 100 for generating structured text content using speech recognition models. The system 100 is an example of a system implemented as computer programs on one or more computers in one or more locations, in which the systems, components, and techniques described below can be implemented.

The system 100 receives acoustic sequences as input and processes received acoustic sequences using a speech recognition model 104 and a prosody model 116 to generate transcriptions of received acoustic sequences and indications of speech prosody 118, respectively. For example, the system 100 can obtain an input acoustic sequence 102 and process the input acoustic sequence 102 using the speech recognition model 104 to generate a transcription 108 of the input acoustic sequence 102. As another example, the system 100 can obtain an input acoustic sequence 102 and process the input acoustic sequence 102 using the prosody model 116 to generate an indication of speech prosody 118 based on the input acoustic sequence 102.

The input acoustic sequence 102 is a digital representation of one or more utterances. For example, the input acoustic sequence 102 may be a sequence of multiple frames of audio data that correspond to a set of time steps, e.g., where each frame of audio data is associated with 10 milliseconds of audio stream data. Each frame of audio data in the sequence of multiple frames of audio data may include feature values for the frame that characterize the utterance at the corresponding time step.

In some cases the input acoustic sequence may be a digital representation of one or more utterances spoken by multiple people. For example, the input acoustic sequence may be a digital representation of a conversation between two or more people.

The speech recognition model 104 processes the input acoustic sequence 102 and generates a transcription 108 of the input acoustic sequence. The speech recognition model 104 can be one of many different types of speech recognition models, e.g., deep neural networks, hidden Markov models or neural transducers. Example speech recognition models are described in more detail below with reference to FIGS. 2 and 3.

The transcription 108 may include a sequence of characters that forms transcription of the one or more utterances represented by the input acoustic sequence 102. For example, the sequence of characters may include characters from an alphabet of alphabetic letters. The alphabet may be a standard set of alphabetic letters which is used to write one or more natural languages, generally because the alphabetic letters represent phonemes in the spoken natural language. For example, the alphabet may be the English alphabet. The character set may also include other characters such as Arabic numerals, a space character, punctuation characters, and an unknown character.

The speech recognition model 104 includes a domain specific acoustic model 106a, domain specific pronunciation model 106b, and a domain specific language model 106c. The domain specific acoustic model 106a generates a domain specific phoneme representation of the acoustic sequence 102. The domain specific pronunciation model 106b generates a domain specific grapheme representation of the acoustic sequence 102 from the domain specific phoneme representation. The domain specific language model 106c assigns probabilities to sentences of domain specific words, i.e., the domain specific language model 106c can include a probability distribution over a sequence of words. Example language models include statistical n-gram language models or recurrent neural network language models.

The domain specific acoustic model 106a may be trained using domain specific training acoustic data, e.g., acoustic data that has been generated or taken from a domain specific knowledge base, with corresponding domain specific transcriptions or domain specific notes. The pronunciation model 106b can either be generated manually or learned from domain-specific acoustic data with corresponding domain-specific transcriptions. The domain-specific language model 106c may be trained using a training corpus of domain specific text, e.g., text from a domain specific knowledge base, text from domain specific transcriptions, and/or text from domain specific notes.

In some implementations the domain specific acoustic model 106a, pronunciation model 106b, and language model 106c may be a medical domain models. For example, a medical language model may be a language model that has been trained to assign probabilities to sentences of words using a corpus of medical text, e.g., text from a medical knowledge base such as medical textbooks, medical transcriptions or medical notes. Other example domain specific language models can include legal language models that have been trained to assign probabilities to sequences of words using corpuses of legal text, business language models that have been trained to assign probabilities to sequences of words using business related text, or finance language models that have been trained to assign probabilities to sequences of words using finance related text.

In some implementations the domain specific language model 106c may be trained using a domain specific corpus of text in a particular language and another corpus of text in the particular language, e.g., a corpus of non-domain specific text in a language that matches the language of the domain specific corpus of text.

The system 100 includes one or more domain specific predictive models. For convenience one domain specific predictive model 110 is shown in FIG. 1, however in some implementations the system 100 may include multiple domain specific predictive models.

The domain specific predictive model 110 receives the generated transcription 108 of the input acoustic sequence 102 and processes the transcription 108 to generate structured text content 114 that is derived from the transcription 108 of the input acoustic sequence 102.

In some implementations, the domain specific predictive model may be a summarization predictive model that is configured to generate a physician note that is derived from the transcription 108 of the input acoustic sequence 102. For example, as described above, the input acoustic sequence may be a digital representation of a conversation between two people, e.g., a medical professional and a patient. In this example, the one or more domain specific predictive models may include a summarization predictive model that generates a physician note that is derived from portions of the transcription 108 of the input acoustic sequence that corresponds to utterances spoken by the medical professional, the patient, or both.

In other implementations, the domain specific predictive model can directly derive the physician note from the input acoustic sequence 102. In some implementations the domain specific predictive model may be configured to derive a physician note using both the input acoustic sequence 102 and past longitudinal medical records data.

The generated physician note may be a document with a particular format, e.g., a document including one or more sections of medical content relating to a patient that are ordered according to a particular order. The physician note may include information that has been extracted from the transcription 108 of the input acoustic sequence 102. For example, the domain specific predictive model 110 may be configured to analyze the received transcription 108 of the input acoustic sequence 102 and extract information from the transcription 108 to include in one or more sections of the formatted physician note, e.g., a patient name, date of medical professional—patient interaction, assessment of patient condition and a discussed treatment plan. In some cases the order of information included in the physician note may differ to the order in which the information was provided or discussed during the conversation between the medical professional and patient. Therefore, extracting information from the transcription 108 of the input acoustic sequence 102 to include in one or more sections of the formatted physician note may include identifying sections of the formatted physician note and extracting information from the transcription 108 to include in the identified sections. The generated physician note may include time stamps referring to the section of audio used to generate that note.

The physician note may include information that has been extracted from the transcription 108 of the input acoustic sequence 102 and augmented. For example, the domain specific model 110 may be configured to analyze the received transcription 108 of the input acoustic sequence 102, extract information from the transcription 108 that is relevant to one or more sections of the formatted physician note and augment the information based on properties of the one or more sections of the formatted physician note. In some cases information provided by a patient in a patient—medical professional conversation may include colloquial terminology, too much or too little detail, or both. Therefore, extracting and augmenting information to include in a physician note may include identifying a section of the formatted physician note, e.g., a patient assessment section, extracting an answer given by the patient in response to a question from the medical professional, e.g., an answer to the question "how are you feeling today?," and reformulating the patient's answer to include an appropriate level of formality and detail. Generating a physician note using a summarization predictive model is described below with reference to FIG. 4.

In some implementations, the domain specific predictive model 110 may be a billing predictive model that is configured to generate a bill based on the transcription 108 of the input acoustic sequence 102. For example, as described above, the input acoustic sequence may be a digital representation of a conversation between two people, e.g., a medical professional and a patient. In these cases, the one or more domain specific predictive models may include a billing predictive model that generates a bill based on portions of the transcription 108 of the input acoustic sequence 102 that correspond to utterances spoken by the medical professional.

For example, the billing predictive model may be configured to analyze a received transcription of an acoustic sequence to identify information relating to costs associated with the conversation between the patient and the medical professional, e.g., a duration of time in which the patient and medical professional were interacting, procedures performed by the medical professional, diagnosis spoken by the medical professional, or medication prescribed by the medical professional. Based on identifying such information, the billing predictive model may determine costs associated with the identified information and generate a bill based on the determined costs. Generating a bill using a billing predictive model is described below with reference to FIG. 4.

In some implementations the domain specific predictive model 110 may be a patient instructions predictive model that is configured to generate patient instructions that are derived from the transcription 108 of the input acoustic sequence 102. For example, as described above, the input acoustic sequence may include a digital representation of a conversation between two people, e.g., a medical professional and a patient. In these cases, the one or more domain specific predictive models may include a patient instructions predictive model that generates patient instructions based on portions of the transcription 108 of the input acoustic sequence 102 that correspond to utterances spoken by the medical professional.

For example, the patient instructions predictive model may be configured to analyze a received transcription of an acoustic sequence to identify instructions given to the patient by the medical professional. Based on identifying such instructions, the patient instructions predictive model may generate instructions for the patient regarding their future treatment. The generated instructions may be provided as a formatted document with clear instructions for the patient. In some cases the instructions given in the generated patient instructions may differ from those in the transcription 108 of the input acoustic sequence 102. For example, during a conversation with a patient a medical professional may use language that is easier to understand, e.g., calling a particular drug or therapy by a common name such as "pain killers," whereas a formal document describing patient instructions may include additional details such as a particular type of pain killer, an amount to be taken and how/when the pain killer is to be taken. Generating patient instructions is described below with reference to FIG. 4.

The prosody model 116 processes the input acoustic sequence 102 and generates an indication of speech prosody 118 based on the input acoustic sequence 102. For example, the prosody model 116 may be configured to analyze the input acoustic sequence 102 to identify portions of the acoustic sequence that represent utterances spoken by the patient. The prosody model 116 may then analyze the portions of the acoustic sequence that represent utterances spoken by the patient to infer various features of the patient, e.g., an emotional state of the patient. Alternatively or in addition, the prosody model 116 may analyze utterances spoken by the patient to infer features of the utterances spoken by the patient, e.g., the form of the utterances, presence of irony or sarcasm, emphasis, contrast or focus. The prosody model may generate an indication of speech prosody 118 based on the inferred features. For example, if the prosody model 116 infers that a patient is in a depressive state the prosody model 116 may generate an indication that the patient may be suffering from depression.

In some implementations the domain specific predictive model 110 may be a speech prosody predictive model that is configured to screen for diseases based on a received indication of speech prosody 118 that has been derived from the input acoustic sequence 102. For example, the speech prosody predictive model may receive an indication of speech prosody 118 that indicates that a patient is in a depressive state. The speech prosody predictive model may then use this information to screen for diseases that may cause depression. In some cases, the speech prosody predictive model may also use a received transcription 108 of the input acoustic sequence 102 in combination with a received indication of speech prosody 118 to screen for diseases.

The speech prosody predictive model may provide, as output, a document listing results from the screening, e.g., a document listing a number of diseases that the patient may be suffering from.

In some implementations the domain specific predictive model 110 may be a translation model that is configured to translate the transcription 108 of the input acoustic sequence 102 into a target language. For example, in some cases a patient and medical professional may converse in a first language, whereas official documentation of the conversation is required to be in a second language. In these cases the translation model may be configured to translate the transcription 108 of the input acoustic sequence 102 from the first language into the second language. In some cases the system may further provide the translation model with the input acoustic sequence 102. Generating a translation of an input acoustic sequence is described below with reference to FIG. 4.

In some implementations the domain specific predictive model 110 may be configured to receive additional data as input, e.g., other predictive model input data 112, and to process received additional data to generate the structured text content 114. Example additional predictive model input data 112 includes but is not limited to (i) the input acoustic sequence 102, (ii) an acoustic sequence representing a physician dictation, or (iii) data representing a patient's medical record. For example, in some implementations the domain specific predictive model 110 may process the received transcription 108 together with one or more of (i) the input acoustic sequence 102, (ii) an acoustic sequence representing a physician dictation, or (iii) data representing a patient's medical record to generate the structured text content 114. In other implementations the domain specific predictive model 110 may process each input separately to generate separate structured text contents that correspond respectively to each processed input, e.g., structured text content relating to a patient's diagnosis, structured text content relating to a patient's progress and structured text content relating to a billing code. Optionally, the separate structured text contents may be combined into final structured text content. Generating structured text content derived from a transcription of an input acoustic sequence and other predictive model input data is described below with reference to FIG. 4.

Figure 2:
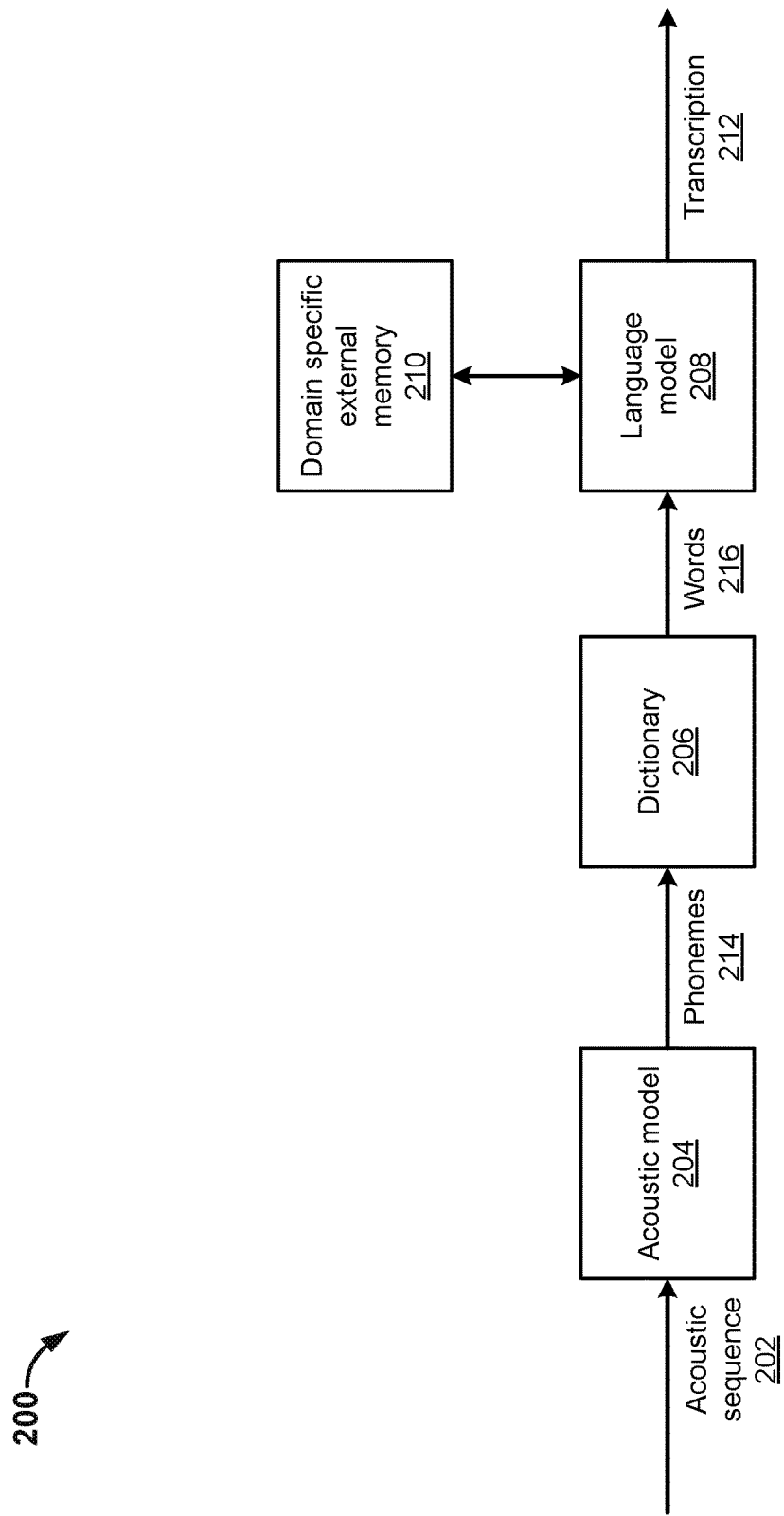
FIG. 2 shows an example automatic speech recognition system.

FIG. 2 shows an example automatic speech recognition system 200. The example automatic speech recognition system 200 includes an acoustic model 204, a dictionary 206, a language model 208 and a domain specific external memory 210.

The example automatic speech recognition system 200 is configured to receive an acoustic sequence 202 as input, where the acoustic sequence represents a sequence of multiple frames of audio data that correspond to a set of time steps. The system 200 may be configured to process the received acoustic sequence 202 using the acoustic model 204, a dictionary 206, a language model 208 and a domain specific external memory 210 to generate a transcription 212 of the utterances represented by the input acoustic sequence 202.

The acoustic model 204 may be configured to process a received acoustic sequence, e.g., acoustic sequence 202, to generate a predicted phoneme representation of the acoustic sequence, e.g., phonemes 214. In some implementations the acoustic model 204 may be a Deep Neural Network (DNN), a Recurrent Neural Network (RNN), a Hidden Markov Model (HMM), or a hybrid DNN-HMM model.

The system 200 may use the dictionary 206 to process phoneme representations of an acoustic sequence, e.g., phonemes 214, to generate one or more words that may represent the acoustic sequence, e.g., words 216. In some implementations the dictionary 206 may include a domain specific dictionary, e.g., a dictionary of words from a specific domain such as a medical dictionary.

The language model 208 may be configured to process one or more words that may represent the acoustic sequence, e.g., words 216, to generate a transcription 212 of the acoustic sequence 202. In some implementations the language model 208 may be in communication with a domain specific external memory, e.g., a medical knowledge base. For example, the language model may be trained to assign probabilities to sentences of received words using a corpus of medical text, e.g., text from a medical knowledge base such as medical textbooks, medical transcriptions or medical notes.

As described above with reference to FIG. 1, the transcription 212 may be provided to one or more domain specific predictive models for further processing. Using domain specific models to process transcriptions of acoustic sequences to generate structured text content, e.g., documents, derived from the transcriptions is described in more detail below with reference to FIG. 4.

Figure 3:
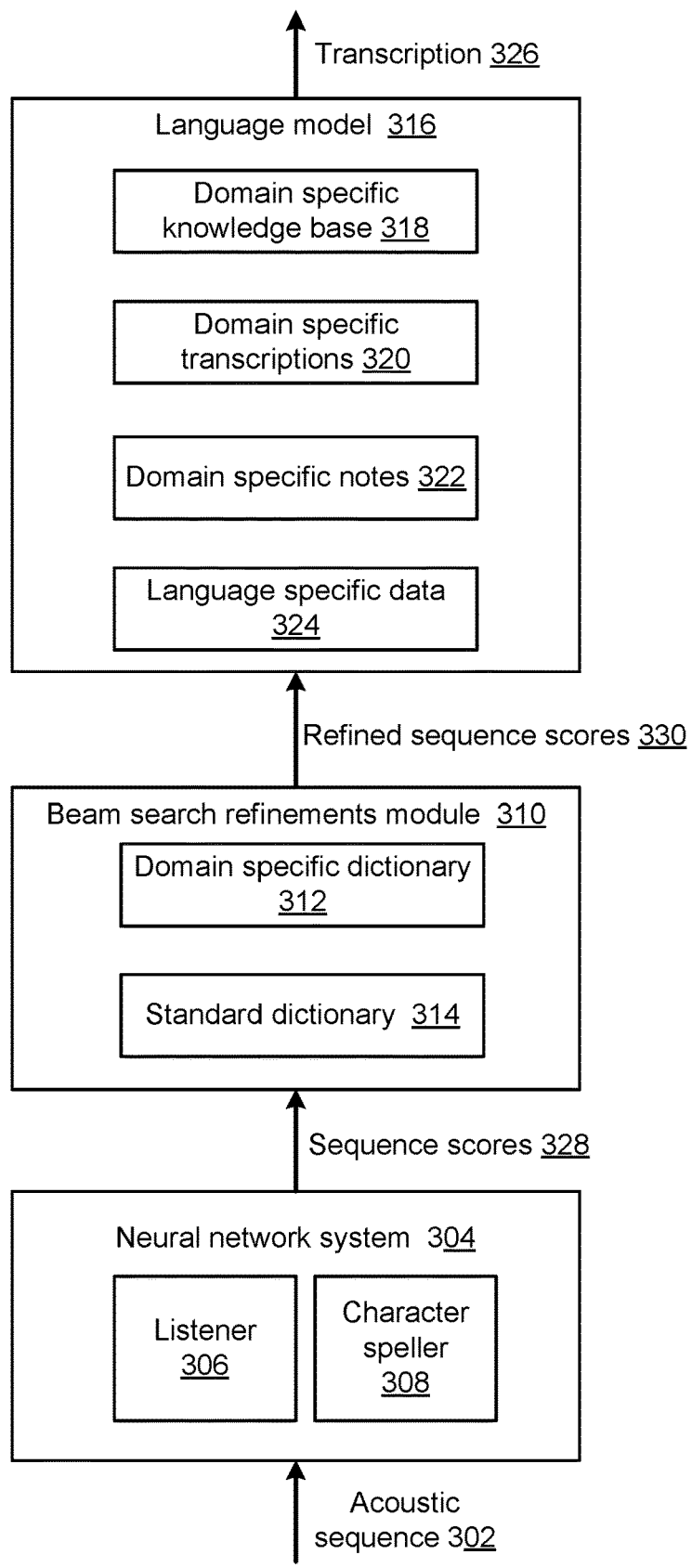
FIG. 3 shows an example end-to-end attention-based speech recognition system.

FIG. 3 shows an example end-to-end attention based speech recognition system 300, as described above with reference to FIG. 1. The example end-to-end attention based speech recognition system 300 includes a neural network system 304, beam search refinements 310 and a language model 316.

As described above with reference to FIG. 1, the example speech recognition system 300 may be configured to receive an acoustic sequence 302 as input, where the acoustic sequence represents a sequence of multiple frames of audio data that correspond to a set of time steps. The system 300 may be configured to process the received acoustic sequence 302 using the neural network system 304, beam search refinements 310 and a language model 316 to generate a transcription 326 of the utterances represented by the input acoustic sequence 302.

The neural network system 304 includes a listener component 306 and a character speller component 308. In some implementations the listener component 306 may be an acoustic sequence encoder that includes a first Recurrent Neural Network (RNN) with a pyramid structure. A RNN with pyramid structure may include a bottom neural network layer and one or more pyramid neural network layers, where at each time step each pyramid layer receives an input from a preceding pyramid layer, or if the pyramid layer is the lowest layer in the sequence of pyramid layers, from the bottom layer. The bottom neural network layer receives the acoustic sequence 302 as input.

The first RNN layers can include one or more Bidirectional Long Short Term Memory (BLSTM) neural network layers. A BLSTM neural network layer is a neural network layer that has one or more LSTM memory blocks and that predicts or labels each element of a sequence based on both the past and the future context of the element. An example BLSTM neural network that can be used to process acoustic sequences is described in more detail in "Hybrid Speech Recognition with Bidirectional LSTM", Alex Graves, Navdeep Jaitly, and Abdel-rahman Mohamed, *Automatic Speech Recognition and Understanding Workshop*, 2013.

The first RNN with a pyramid structure may be configured to process a received acoustic sequence for a time step using first RNN layers to generate an alternative representation for the acoustic sequence. For example, the first RNN with pyramid structure may concatenate outputs at consecutive steps of each pyramid layer before providing an output to the next layer, e.g., the first RNN with a pyramid structure may concatenate the output h of a j-1th pyramid BLSTM layer at consecutive steps 2i and 2i+1. In each successive stacked pyramid RNN layer, the time resolution may therefore be reduced. For example, the time resolution may be reduced $2^l$ times, where l is the number of pyramid layers stacked on top of the bottom layer.

In some implementations the character speller component 308 may be an attention-based decoder. An attention-based decoder may include a second RNN that receives an input sequence and maintains an internal state while processing inputs in a received input sequence. In particular, the second RNN may use some or all of the internal hidden state of the network from processing a preceding input in the input sequence in combination with the current input in the input sequence to update the internal hidden state of the recurrent neural network. For example, at each time step, the second RNN may receive as input a preceding sequence of characters, e.g., a character output at the time step preceding the current time step, and a preceding context vector, e.g., a context vector corresponding to the time step preceding the current time step. The second RNN may process the preceding sequence of characters and the preceding context vector to generate as output an updated hidden state of the second RNN for the time step, i.e., to update its internal hidden state.

A context vector generator component may receive as input the updated hidden state of the second RNN at the time step and the alternative representation described above. The context vector generator component may process the updated hidden state of the second RNN at the time step and the alternative representation to generate as output a context vector for the time step. The context vector generator component may provide the generated context vector for the time step to a sequence score neural network, e.g., a Multi-Layer Perceptron (MLP) with softmax outputs. The sequence score neural network may process the context vector for the time step and the updated hidden state of the second RNN to generate as output a set of sequence scores 328 for the time step. Each sequence score corresponds to a respective sequence of characters. For example, as described above, the characters may include a set of alphabetic letters which is used to write one or more natural languages, e.g., the English alphabet. The characters may also include Arabic numerals, a punctuation characters, and an unknown character. The score for a given sequence represents a likelihood that the corresponding sequence is the current sequence at the time step in an output sequence that is a transcription of the input acoustic sequence 302.

The beam search refinements module 310 may receive and process the sequence scores 328 for each time step to refine the sequence scores and generate as output refined sequence scores 330. For example, the beam search refinements module 310 may include a domain specific dictionary 312 and a standard dictionary 314 that are used to select one or more top scoring sequence scores 330 for each time step, e.g., according to the structure of the sequences.

The language model 316 may receive and process the refined sequence scores 330 for each time step to determine a character sequence that represents a transcription 326 of the input acoustic sequence 302, as described above with reference to FIG. 1. For example, for each time step, the system 300 may select a highest scoring sequence of characters from the refined sequence scores to determine a transcription 326 of the input acoustic sequence 302. The language model 316 may use one or more of a domain specific knowledge base 318, domain specific transcriptions 320, domain specific notes 322 or language specific data 324 to determine the transcription 326, as described above with reference to FIG. 1.

As described above with reference to FIG. 1, the transcription 326 may be provided to one or more domain specific predictive models for further processing. Using domain specific models to process transcriptions of acoustic sequences to generate structured text content, e.g., documents, derived from the transcriptions is described in more detail below with reference to FIG. 4.

Figure 4:
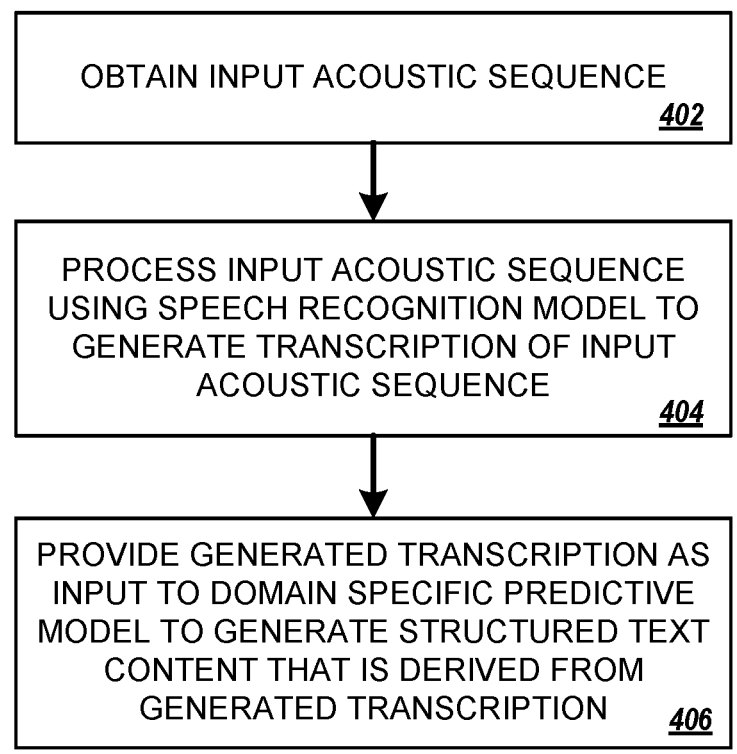
FIG. 4 is a flow diagram of an example process for generating structured text content derived from a transcription of an input acoustic sequence.

FIG. 4 is a flow diagram of an example process 400 for generating structured text content derived from a transcription of an input acoustic sequence. For convenience, the process 400 will be described as being performed by a system of one or more computers located in one or more locations. For example, a speech recognition system including one or more domain specific predictive models, e.g., system 100 of FIG. 1, appropriately programmed, can perform the process 400.

The system obtains an input acoustic sequence (step 402). The input acoustic sequence represents one or more utterances. For example, the input acoustic sequence may represent a conversation between two or more people, e.g., a conversation between a patient and a healthcare professional.

The system processes the input acoustic sequence using a speech recognition model to generate a transcription of the input acoustic sequence (step 404). The speech recognition model includes a domain-specific language model, that is a language model that has been trained to generate probability distributions over sequences of words using a domain-specific corpus of text. In some cases the domain-specific language model may be trained using a domain-specific corpus of text and a corpus of text in a particular language, e.g., a corpus of non-domain-specific text in a language that matches the language of the domain-specific corpus of text.

Example domain-specific language models include a medical language model, legal language model, or business language model. Continuing the example above, the domain-specific language model may include a medical language model that has been trained using medical-specific training data. For example, the medical language model may have been trained using medical related text, e.g., text from a medical knowledge base such as medical textbooks, medical transcriptions or medical notes.

The system provides the generated transcription of the input acoustic sequence as input to a domain-specific predictive model to generate structured text content that is derived from the transcription of the input acoustic sequence (step 406).

Continuing the example above, in some implementations the domain-specific predictive model includes a summarization predictive model that is configured to generate a physician note that is derived from the transcription of the input acoustic sequence. Generally, a physician note includes a document that records details to document a patient's clinical status during the course of hospitalization or over the course of outpatient care. For example, a physician note may be generated each time a healthcare professional has an interaction with a patient.

A physician note should be organized, easily understood, complete, accurate and concise. Therefore, in some implementations the physician note generated by the system may include a document with a particular format. For example, the generated physician note may be organized into one or more sections, e.g., a descriptive section detailing a patient's personal details and the date and time of the interaction, an assessment section detailing the physician's assessment of the patient's current condition, and a treatment section detailing the physician's recommended treatment plan. In these cases the summarization predictive model may be configured to populate sections of the physician note with relevant information taken from the transcription of the conversation between the patient and the healthcare professional. The resulting physician note may therefore be better organized and easier to understand than the transcription itself.

In addition, in some implementations the physician note generated by the system may include information that the summarization predictive model has extracted from the transcription of the input acoustic sequence based on the document format. For example, the transcription of the conversation between the patient and the healthcare professional may include a large amount of information that is not relevant to the physician note, e.g., small talk, repetitions or patient questions. In these cases the summarization predictive model may be configured to analyze the transcription of the conversation between the patient and the healthcare provider and extract relevant information to include in the generated physician note.

For example, the transcription of the conversation between the patient and the healthcare professional may include a sentence where the patient conversationally describes their current level of pain or discomfort, e.g., "well sometimes I think it is worse than other times, like in the mornings it can be worse. Generally, though, I would say it is bearable." In this example, the system may identify that the patient is describing their current level of pain, e.g., by identifying that the healthcare professional enquired after the current level of pain, and extract the information "pain bearable" from the transcription. The resulting physician note may therefore be more easy to understand and concise than the transcription itself.

Furthermore, in some implementations the physician note generated by the system may include information that the summarization predictive model has extracted from the transcription of the input acoustic sequence and augmented based on the document format. For example, the transcription of the conversation between the patient and the healthcare professional may include information that is not complete or uses acronyms. In these cases the summarization predictive model may be configured to analyze the transcription of the conversation between the patient and the healthcare provider to identify important information, and to augment information to include in the generated physician note.

For example, in some cases the transcription of the conversation between the patient and the healthcare professional may include a sentence where the patient colloquially expresses their treatment wishes, e.g., "I don't want anything that will make me feel sick." In this example, the system may identify that the patient is expressing their feelings towards a particular treatment proposal, e.g., by identifying that the healthcare professional explained potential treatment plans to the patient, and augment the patient response such that the generated physician note includes the information "The patient does not wish to pursue the use of drug X."

As another example, in some cases the transcription of the conversation between the patient and the healthcare professional may include one or more acronyms. In this example, the system may identify the acronym and augment the acronym such that the generated physician note includes the full unabbreviated word or phrase.

In some cases the input acoustic sequence representing one or more utterances may not capture all the necessary information needed to generate structured text content that is derived from the transcription of the input acoustic sequence. For example, in some cases a conversation between a patient and a healthcare professional may not include all necessary information to generate a physician note summarizing the patient-healthcare professional interaction. In these cases the summarization predictive model may be further configured to generate a physician note that is derived from the transcription of the input acoustic sequence and one or more of (i) the input acoustic sequence, (ii) data associated with the input acoustic sequence, (iii) an acoustic sequence representing a physician dictation, or (iv) data representing a patient's medical record.

For example, the system may use data associated with the input acoustic sequence to populate sections of the physician note, e.g., a time and date of the interaction between the patient and the healthcare professional. As another example, the system may use an acoustic sequence representing a physician dictation to identify more precise information regarding the interaction, e.g., a precise assessment of the patient's condition using medical terminology that might not have been used or discussed during the patient-healthcare professional interaction, or a precise description of a proposed treatment plan. As a further example, the system may use data representing a patient's medical record to identify supplementary information to include in the physician note.

As described above with reference to FIG. 1, in some implementations the domain-specific predictive model may include an automated billing predictive model that is configured to generate a bill based on the transcription of the input acoustic sequence. In cases where the input acoustic sequence represents a conversation between a patient and a healthcare professional, the system may use an automated billing predictive model to generate a bill based on the transcription of the conversation. The generated bill may include a formatted document that is organized into one or sections or fields. For example, the generated bill may include a summary of an interaction between a patient and a healthcare professional, as well as a cost associated with the interaction between the patient and the healthcare professional. In these cases, the automated billing predictive model may be configured to populate a section of the bill with a summary of an interaction between a healthcare professional and patient and to generate a cost associated with the interaction.

In some cases the input acoustic sequence representing one or more utterances may not capture all the necessary information needed to generate structured text content that is derived from the transcription of the input acoustic sequence. For example, in some cases a conversation between a patient and a healthcare professional may not include all the necessary information needed to generate a bill that is associated with the patient-healthcare provider interaction. In these cases the automated billing predictive model may be further configured to generate a bill that is based on the transcription of the input acoustic sequence and one or more of (i) the input acoustic sequence, (ii) data associated with the input acoustic sequence, (iii) an acoustic sequence representing a physician dictation, or (iv) data representing a patient's medical record.

For example, a generated bill may be required to include a date of an interaction between the patient and the healthcare professional and the names of the patient and the healthcare professional. In this example the system may use data associated with the input acoustic sequence to identify a time and date of the conversation, and to identify any participants of the conversation. As another example, the system may use an acoustic sequence representing a physician dictation to identify more precise information regarding the interaction to include in the bill, e.g., a precise description or name of prescribed medicine. As a further example, the system may use data representing a patient's medical record to identify supplementary information to include in the physician note or to generate a cost associated with the interaction.

As described above with reference to FIG. 1, in some implementations the domain-specific predictive model may include a patient instruction predictive model that is configured to generate patient instructions that are derived from the transcription of the input acoustic sequence. In cases where the input acoustic sequence represents a conversation between a patient and a healthcare professional, the system may use a patient instruction predictive model to generate patient instructions based on the transcription of the conversation. For example, the system may identify portions of the transcription that correspond to utterances spoken by the physician to extract patient instructions.

In some cases the input acoustic sequence representing one or more utterances may not capture all the necessary information needed to generate patient instructions. In these cases the patient instruction predictive model may be further configured to generate patient instructions that are derived from the transcription of the input acoustic sequence and one or more of (i) the input acoustic sequence, (ii) data associated with the input acoustic sequence, (iii) an acoustic sequence representing a physician dictation, or (iv) data representing a patient's medical record.

For example, patient instructions may be required to include a date of an interaction between the patient and the healthcare professional. In this example the system may use data associated with the input acoustic sequence to identify a time and date of the conversation. As another example, the system may use an acoustic sequence representing a physician dictation to identify information regarding patient instructions that is more precise than those discussed during the conversation between the patient and the healthcare professional.

As described above with reference to FIG. 1, in some implementations the system may include a speech prosody detection predictive model. In these implementations the system may further provide the input acoustic sequence as input to the speech prosody detection predictive model to generate an indication of speech prosody that is derived from the input acoustic sequence. For example, the system may use the speech prosody detection predictive model to screen for diseases that can affect the prosody of speech, e.g., depression or neurodegenerative diseases.

As described above with reference to FIG. 1, in some implementations the domain-specific predictive model may include a translation model that is configured to translate the transcription of the input acoustic sequence into a target language. In these implementations the system may further provide the input acoustic sequence and/or the generated transcription of the input acoustic sequence to the translation model to generate a translation of the input acoustic sequence into a target language.

For convenience, steps 402-406 described above have been discussed using examples relating to a medical-specific domain. However, steps 402-406 may be applied to other domain-specific settings, such as business settings, legal settings, financial settings, or any setting in which converting a conversation between multiple people to written notes and using said notes to generate structured text content, e.g., documents, is beneficial.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non transitory program carrier for execution by, or to control the operation of, data processing apparatus. Alternatively or in addition, the program instructions can be encoded on an artificially generated propagated signal, e.g., a machine-generated electrical, optical, or electromagnetic signal, that is generated to encode information for transmission to suitable receiver apparatus for execution by a data processing apparatus. The computer storage medium can be a machine-readable storage device, a machine-readable storage substrate, a random or serial access memory device, or a combination of one or more of them. The computer storage medium is not, however, a propagated signal.

The term "data processing apparatus" encompasses all kinds of apparatus, devices, and machines for processing data, including by way of example a programmable processor, a computer, or multiple processors or computers. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, or a combination of one or more of them.

A computer program (which may also be referred to or described as a program, software, a software application, a module, a software module, a script, or code) can be written in any form of programming language, including compiled or interpreted languages, or declarative or procedural languages, and it can be deployed in any form, including as a stand alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub programs, or portions of code. A computer program can be deployed to be executed on one computer or on multiple computers that are located at one site or distributed across multiple sites and interconnected by a communication network.

As used in this specification, an "engine," or "software engine," refers to a software implemented input/output system that provides an output that is different from the input. An engine can be an encoded block of functionality, such as a library, a platform, a software development kit ("SDK"), or an object. Each engine can be implemented on any appropriate type of computing device, e.g., servers, mobile phones, tablet computers, notebook computers, music players, e-book readers, laptop or desktop computers, PDAs, smart phones, or other stationary or portable devices, that includes one or more processors and computer readable media. Additionally, two or more of the engines may be implemented on the same computing device, or on different computing devices.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Computers suitable for the execution of a computer program include, by way of example, can be based on general or special purpose microprocessors or both, or any other kind of central processing unit. Generally, a central processing unit will receive instructions and data from a read only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A computer implemented method comprising:
obtaining an input acoustic sequence, the input acoustic sequence representing one or more utterances;
processing the input acoustic sequence using a speech recognition model to generate a transcription of the input acoustic sequence; and
providing the generated transcription of the input acoustic sequence as input to a domain-specific predictive model to generate structured text content, wherein the domain-specific predictive model comprises a patient instructions predictive model configured to generate patient instructions based on at least a portion of the transcription of the input acoustic sequence that corresponds to utterances spoken by a medical professional, wherein the patient instructions include instructions regarding a future treatment for a patient.

2. The method of claim 1, wherein the input acoustic sequence includes a digital representation of a conversation between a medical professional and a patient.

3. The method of claim 1, wherein the patient instruction predictive model is further configured to generate patient instructions that are derived from the transcription of the input acoustic sequence and one or more of (i) the input acoustic sequence, (ii) data associated with the input acoustic sequence, (iii) an acoustic sequence representing a physician dictation, or (iv) data representing a patient's medical record.

4. The method of claim 1, wherein the speech recognition model comprises a domain-specific language model.

5. The method of claim 4, wherein the domain-specific language model comprises a medical language model that has been trained using medical-specific training data.

6. The method of claim 1, wherein the domain-specific predictive model comprises an automated billing predictive model that is configured to generate a bill based on the transcription of the input acoustic sequence.

7. The method of claim 6, wherein the automated billing predictive model is further configured to generate a bill that is based on the transcription of the input acoustic sequence and one or more of (i) the input acoustic sequence, (ii) data associated with the input acoustic sequence, (iii) an acoustic sequence representing a physician dictation, or (iv) data representing a patient's medical record.

8. The method of claim 1, further comprising providing the input acoustic sequence as input to a speech prosody detection predictive model configured to process the input acoustic sequence to generate an indication of speech prosody that is derived from the input acoustic sequence.

9. The method of claim 8, further comprising screening for diseases based on the generated indication of speech prosody.

10. The method of claim 9, wherein the speech prosody detection predictive model is configured to provide, as output, a document listing results from the screening.

11. The method of claim 1, wherein the domain-specific predictive model comprises a translation model that is configured to translate the transcription of the input acoustic sequence into a target language.

12. The method of claim 11, wherein the translation model is further configured to translate the transcription of the input acoustic sequence into a target language using the input acoustic sequence.

13. A system comprising one or more computers and one or more storage devices storing instructions that are operable, when executed by the one or more computers, to cause the one or more computers to perform operations comprising:

obtaining an input acoustic sequence, the input acoustic sequence representing one or more utterances;

processing the input acoustic sequence using a speech recognition model to generate a transcription of the input acoustic sequence; and providing the generated transcription of the input acoustic sequence as input to a domain-specific predictive model to generate structured text content, wherein the domain-specific predictive model comprises a patient instructions predictive model configured to generate patient instructions based on at least a portion of the transcription of the input acoustic sequence that corresponds to utterances spoken by a medical professional, wherein the patient instructions include instructions regarding a future treatment for a patient.

14. The system of claim 13, wherein the patient instruction predictive model is further configured to generate patient instructions that are derived from the transcription of the input acoustic sequence and one or more of (i) the input acoustic sequence, (ii) data associated with the input acoustic sequence, (iii) an acoustic sequence representing a physician dictation, or (iv) data representing a patient's medical record.

15. The system of claim 13, wherein the speech recognition model comprises a domain specific language model.

16. The system of claim 13, wherein the speech recognition model comprises a hybrid deep neural network—hidden Markov model automatic speech recognition model.

17. The system of claim 13, wherein the speech recognition model comprises an end-to-end speech recognition model with attention.

18. One or more non-transitory computer-readable storage media comprising instructions stored thereon that are executable by one or more processing devices and upon such execution cause the one or more processing devices to perform operations comprising:

obtaining an input acoustic sequence, the input acoustic sequence representing one or more utterances;

processing the input acoustic sequence using a speech recognition model to generate a transcription of the input acoustic sequence; and providing the generated transcription of the input acoustic sequence as input to a domain-specific predictive model to generate structured text content, wherein the domain-specific predictive model comprises a patient instructions predictive model configured to generate patient instructions based on at least a portion of the transcription of the input acoustic sequence that corresponds to utterances spoken by a medical professional, wherein the patient instructions include instructions regarding a future treatment for a patient.

19. The one or more non-transitory computer-readable storage media of claim 18, wherein the input acoustic sequence includes a digital representation of a conversation between a medical professional and a patient.

20. The one or more non-transitory computer-readable storage media of claim 18, wherein the domain-specific predictive model comprises a translation model that is configured to translate the transcription of the input acoustic sequence into a target language.

* * * * *